United States Patent [19]

Cassidy

[11] Patent Number: 5,319,170
[45] Date of Patent: Jun. 7, 1994

[54] INDUCTION FLUID HEATER UTILIZING A SHORTED TURN LINKING PARALLEL FLOW PATHS

[75] Inventor: David E. Cassidy, Chelmsford, Mass.

[73] Assignee: Belmont Instrument Corporation, Billerica, Mass.

[21] Appl. No.: 964,079

[22] Filed: Oct. 20, 1992

[51] Int. Cl.⁵ .................................................. H05B 6/10
[52] U.S. Cl. .................................. 219/630; 219/676; 219/667
[58] Field of Search ............. 219/10.51, 10.65, 10.491, 219/10.77, 10.79

[56] References Cited

U.S. PATENT DOCUMENTS

| | | | |
|---|---|---|---|
| 1,656,518 | 1/1928 | Hammers | 219/10.51 |
| 2,494,716 | 1/1950 | McMahon et al. | 219/10.65 |
| 2,550,584 | 4/1951 | Mittelmann | 219/10.51 |
| 3,046,378 | 7/1962 | Holz | 219/10.51 |
| 3,315,681 | 4/1967 | Poppendiek | 128/399 |
| 3,388,230 | 6/1968 | Cunningham et al. | 219/10.51 |
| 3,518,393 | 6/1970 | Besseling et al. | 219/10.65 |
| 3,641,302 | 2/1972 | Sargeant | 219/10.65 |
| 3,812,315 | 5/1974 | Martin | 219/10.65 |
| 3,816,687 | 6/1974 | Heitner | 219/10.491 |
| 4,032,740 | 6/1977 | Mittelmann | 219/10.77 |
| 4,089,176 | 5/1978 | Ashe | 219/10.51 |
| 4,341,936 | 7/1982 | Virgin | 219/10.51 |
| 4,511,777 | 4/1985 | Gerard | 219/10.51 |
| 4,560,849 | 12/1985 | Migliori et al. | 219/10.51 |
| 4,602,140 | 7/1986 | Sobolewski | 219/10.51 |
| 4,638,135 | 1/1987 | Aoki | 219/10.77 |
| 4,855,552 | 8/1989 | Marceau et al. | 219/10.51 |
| 5,003,145 | 3/1991 | Nolle et al. | 219/10.491 |

Primary Examiner—Philip H. Leung
Attorney, Agent, or Firm—George W. Neuner; Henry D. Pahl, Jr.

[57] ABSTRACT

In the fluid heater disclosed herein, a plurality of thin or ribbon-like conductors are embedded in and link a pair of similar flow paths. An inductor is magnetically coupled to the conductors and is energized with alternating current thereby to induce local currents in the conductors and generate heat which is imparted to fluid passing through the flow paths and over the surfaces of the conductors.

8 Claims, 2 Drawing Sheets

INDUCTION FLUID HEATER UTILIZING A SHORTED TURN LINKING PARALLEL FLOW PATHS

BACKGROUND OF THE INVENTION

The present invention relates to apparatus for heating a fluid and more particularly to apparatus for quickly and controllably heating flows of fluids such as blood plasma which may be needed for infusion into a hemorrhaging patient.

A major cause of death in military combat is rapid hemorrhage. To treat hemorrhaging, it is often necessary to quickly infuse a substantial volume of fluid, e.g. whole blood, plasma or blood substitute, so as to maintain an adequate blood volume and circulation. However, to preserve them, such materials are typically refrigerated and it is necessary to warm them before infusion so as to avoid shock to the patient's system. While it is desired to heat the infusate quickly, the temperatures of surfaces in contact with the infusate should not exceed 40-42 degrees C. since, at higher temperatures, protein denaturation and red cell damage can occur. It is also important that any electrical power or potentials utilized in the heating process be effectively isolated from the patient.

Most prior art blood heaters utilize a relatively large water bath reservoir which is preheated to 39-40 degrees C. The water is pumped rapidly through a heat exchanger through which the infusate is perfused, the two fluids typically being separated by a thin, usually metallic, heat exchange surface. These prior art devices are relatively large and cumbersome due to the need for the water bath and water pump as well as the heat exchanger and associated conduits. Such devices accordingly have not been suitable for use in the field either in combat or emergency situations.

Among the objects of the present invention may be noted the provision of novel fluid heating apparatus; the provision of such apparatus which is highly compact; the provision of such apparatus which is easily transportable and which can be operated from battery power; the provision of such apparatus which is highly efficient; the provision of such apparatus which does not require a water bath reservoir; the provision of such apparatus which does not require a substantial warmup period; the provision of such apparatus which provides accurate temperature control; the provision of intrinsic electrical insulation between the heat exchanging element and the power source; the provision of a heat exchanger which is easily removed for replacement without making or breaking electrical power connections; the provision of such apparatus which does not waste substantial quantities of the fluid being heated; the provision of such apparatus which is highly reliable and which is of relatively simple and inexpensive construction. Other objects and features will be in part apparent and in part pointed out hereinafter.

SUMMARY OF THE INVENTION

The fluid heating apparatus of the present invention employs a conduit providing, between an inlet and an outlet, a pair of similar flow paths with an opening between them. Within the conduit, a plurality of thin or ribbon-like conductors parallel each other in closely spaced relationship with each conductor passing through both of the flow paths so as to form an electrically shorted turn linking the opening between the flow paths. An inductor is magnetically coupled to the conductors and is energized with alternating current thereby to induce local currents in the conductors generating heat which is then imparted to the fluid passing over those conductors.

BRIEF DESCRIPTION OF THE PREFERRED EMBODIMENT

Figure 1:
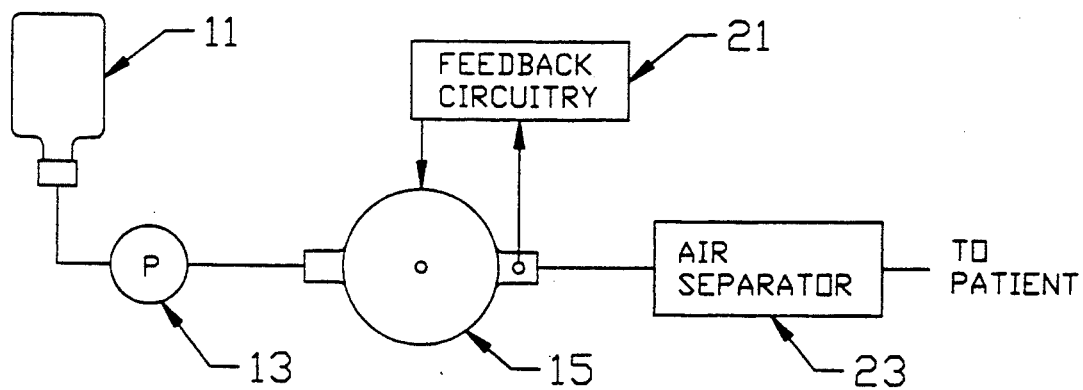
FIG. 1 is a schematic block diagram of fluid heating apparatus according to the present invention.

Referring now to FIG. 1, a reservoir of infusate, e.g. a bag of blood, plasma or other solution, is designated by reference character 11. Infusate drawn from reservoir 11 is driven by a pump 13 through an inductive heater constructed in accordance with the present invention and designated generally by reference character 15.

In the heater 15, infusate is brought to a preselected temperature, control of the temperature being effected by feedback circuitry. The feedback circuitry is designated generally by reference character 21 and responds to outlet temperature, e.g. as sensed by a thermocouple 51 to control the energization of an inductor which effects the generation of heat in the heater 15. This feedback circuitry is described in greater detail hereinafter. From the heater 15, the infusate passes through a separator 23 which removes any possible entrained air bubbles and then passes to the patient.

Figure 2:
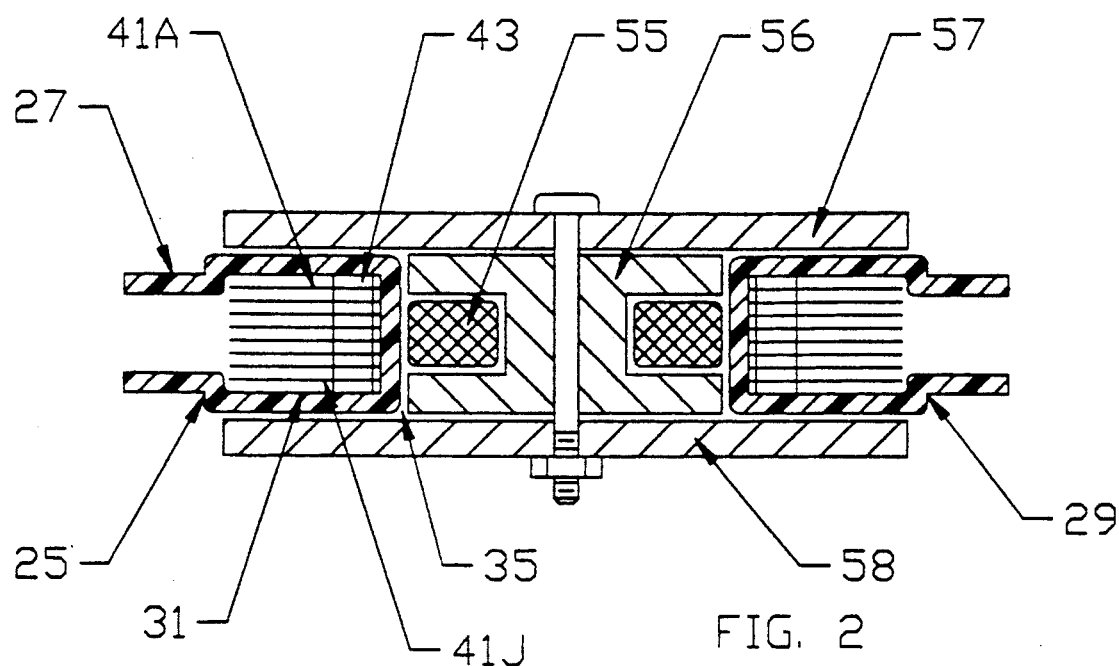
FIG. 2 is a cross-sectional view of an inductive heater employed in the apparatus of FIG. 1.
Figure 3:
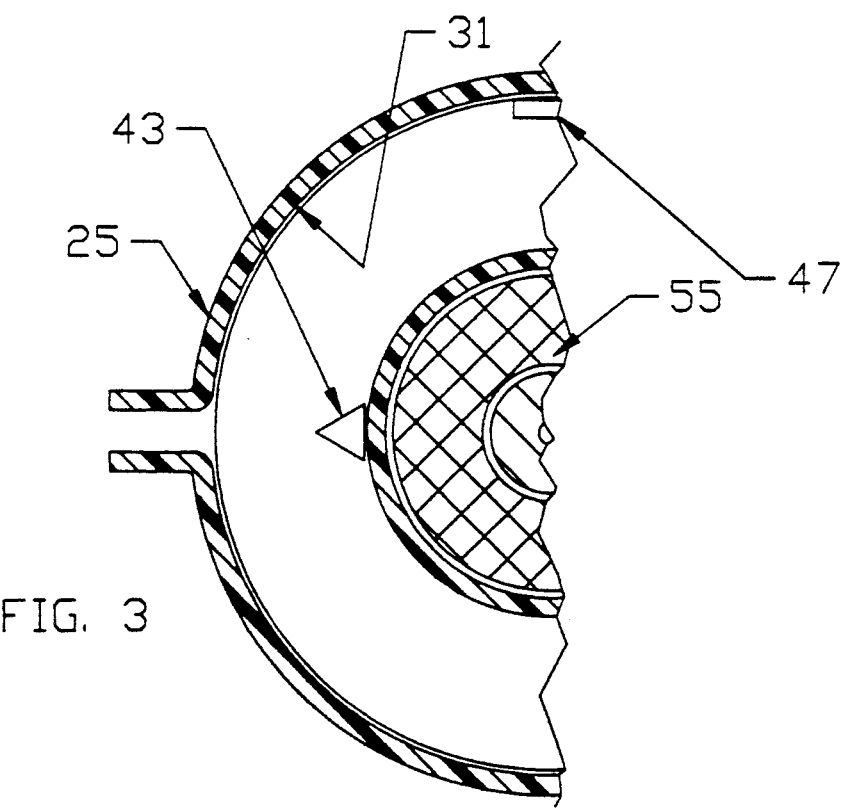
FIG. 3 is a plan view, with parts broken away, of the heater of FIG. 2 taken substantially on the line 3—3 of FIG. 2.

As is illustrated in greater detail in FIGS. 2 and 3, the heater 15 involves a conduit or housing 25 which may be constructed of a suitable plastic material. The housing 25 provides an inlet 27 and an outlet 29 which are connected by a ring-like annular chamber 31 which defines two similar or complementary flow paths connecting the inlet 27 to the outlet 29 with an opening 35 between the flow paths. As each of the two paths connects the inlet to the outlet, they are hydraulically in parallel. While the paths are shown as forming a circle, it should be understood that other shapes could also be used, e.g. ovoid.

Within the chamber 31, are a plurality of thin or ribbon-like conductors 41A–41J. As illustrated, the conductors are in the shape of circular rings but, again, other shapes could be used. The conductors extend generally parallel to each other in spaced relationship with each conductor passing through both of the complementary flow paths so as to form an electrically shorted turn linking the opening 35. As will be apparent, fluid flowing between the inlet 27 and outlet 29 will pass through the spaces between the rings 41A–41J and will be in intimate thermal contact therewith. The rings 41A–41J may, for example, be constructed of soft copper with a suitable coating such as polyurethane to prevent any chemical interaction with the infusate. Other conductive materials such as conductive plastics might also be used.

In the embodiment illustrated, the chamber 31 is circular and the conductors 41A–41J are correspondingly formed as flat rings. This shape simplifies the obtaining of symmetry and even heating but is not necessary to the mode of inductive heating of the present invention. Spacing between adjacent rings 41A–41J is maintained by triangular rubber spacers 43 opposite the inlet and outlet which also aid in smoothly dividing the fluid flow paths and by small spacers 47 at the edges on each side of the rings.

As indicated previously, each of the rings 41A–41J essentially forms a shorted turn linking the central opening 35. An inductor comprising a winding 55 wound on a ferrite bobbin core 56 generates magnetic flux passing through the central opening and thus is inductively coupled to the rings 41A–41J for inducing local currents therein. The winding, however, does not surround either of the flow paths. To improve the degree of coupling between the winding 55 and the rings 41A–41J, ferrite magnetic end plates 57 and 58 may be employed to extend the flux coverage.

Figure 4:
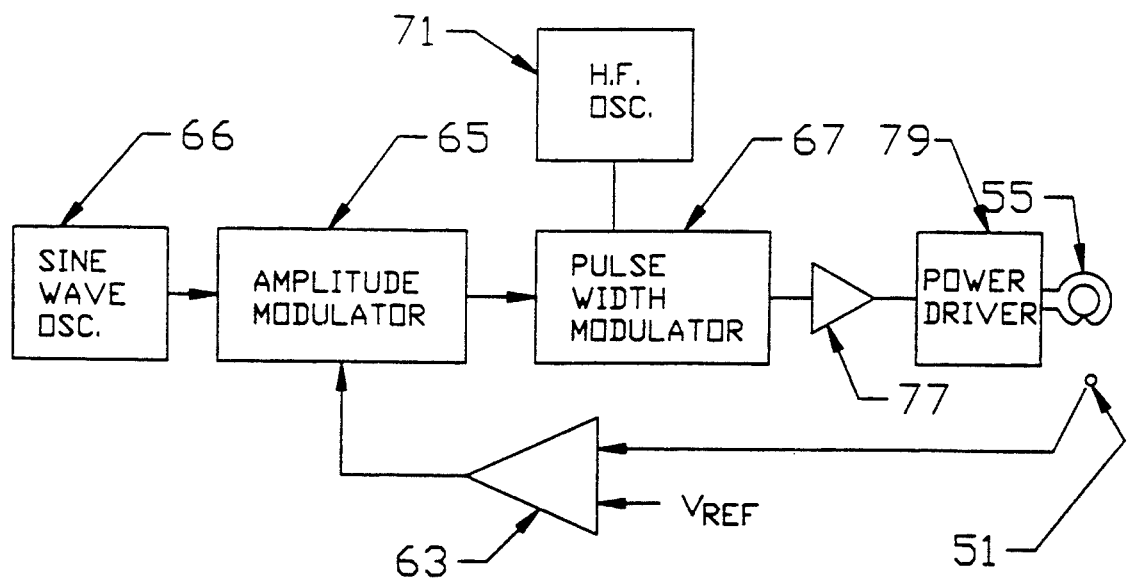
FIG. 4 is a schematic block diagram of circuitry for energizing the inductive heater of FIGS. 2 and 3.

As indicated previously, the energy inductively coupled to the rings 41A–41J is preferably controlled to maintain a preselected temperature at the outlet of the heater. Circuitry suitable for this purpose is illustrated in FIG. 4. The thermocouple 51 provides an output signal corresponding to the temperature at the outlet of the heater. This temperature signal is compared with a reference voltage representing a desired temperature, e.g. 42 degrees C., by an error amplifier designated generally by reference character 63.

The error signal obtained from the error amplifier 63 is applied to a modulator 65 which varies the amplitude cycle of a low frequency signal obtained from a sine wave oscillator 66. This amplitude modulated signal is in turn pulse width modulated, as indicated at 67 by a high frequency signal obtained from an oscillator 71. This results in a signal or waveform having a high frequency carrier but with an energy content proportional to the low frequency amplitude. This signal is in turn applied through suitable driver circuitry 77 to a bridge type power output circuit designated by reference character 79 which provides alternating current energization of the inductor winding 55.

As will be understood by those skilled in the art, the power transferred to the rings 41A–41J will be determined essentially by the average power content of the waveform applied to the winding 55 and thus this power will be modulated in accordance with the error signal in a sense tending to hold the temperature at the output of the heater at a value substantially equal to the desired or set point temperature. Further, since the heat is generated in the rings 41A–41J themselves which are in intimate thermal contact with the fluid passing through the heater, a very high overall efficiency is obtained, e.g. in the order of 88%. Further, since the volume of fluid within the heater at any given moment is relatively small as compared with prior art devices, a relatively quick response is obtained and very little fluid is lost or unavailable to the patient since the volume required to fill the system is correspondingly small. Likewise, only a small part of the system needs to be disposable or replaceable from use to use. All of the electronics, energizing inductor and magnetic cores can be used repeatedly and only the conduit or housing 31 needs to be replaced with its simple and inexpensive ring conductor heating element.

In view of the foregoing it may be seen that several objects of the present invention are achieved and other advantageous results have been attained.

As various changes could be made in the above constructions without departing from the scope of the invention, it should be understood that all matter contained in the above description or shown in the accompanying drawings shall be interpreted as illustrative and not in a limiting sense.

What is claimed is:

1. Apparatus for heating a fluid, said apparatus comprising:
   conduit means providing, between an inlet and an outlet, a pair of complementary flow paths which are hydraulically in parallel with an opening therebetween;
   within said conduit means, a plurality of conductors in closely space relationship with each conductor passing through both of said flow paths and forming an electrically shorted turn linking said opening;
   means for coupling a fluid flow through said conduit means from said inlet to said outlet;
   an inductor providing a winding which, when energized, generates magnetic flux passing through said opening, which winding does not surround either of said flow paths;
   means for energizing said inductor with alternating current thereby to induce local currents in said conductors and generate heat.

2. Apparatus for heating a fluid, said apparatus comprising:
   conduit means providing, between an inlet and an outlet, a pair of similar flow paths which are hydraulically in parallel with an opening therebetween;
   within said conduit means, a plurality of ribbon-like conductors which parallel each other in closely spaced relationship with each conductor passing through both of said flow paths and forming an electrically shorted turn linking said opening;
   means for coupling a fluid flow thorough said conduit means from said inlet to said outlet with the fluid passing thorough the spaces between said conductors;
   an inductor providing a winding which, when energized, generates magnetic flux passing through said openings, which winding does not surround either of said flow paths thereby allowing said conduit means to be removed intact;
   means for energizing said inductor with alternating current thereby to induce local currents in said conductors and generate heat which is imparted to the fluid passing over said conductors.

3. Apparatus as set forth in claim 2 wherein said flow paths are complementary and together form a circular chamber with said inlet at one side and said outlet at the opposite side.

4. Apparatus as set forth in claim 3 wherein said conductors are flat rings aligned with each other and spaced in parallel planes.

5. Apparatus as set forth in claim 4 wherein said rings are separated by triangular spacers adjacent said inlet and outlet which also serve to divide the fluid flow.

6. Apparatus as set forth in claim 2 including means for sensing the temperature at said outlet and means for varying the level of energization of said inductor as a function of the sensed temperature.

7. Apparatus as set forth in claim 6 wherein said level of energization is varied by pulse width modulation of the alternating current energizing said inductor.

8. Apparatus for heating a fluid, said apparatus comprising:

conduit means providing, between an inlet and an outlet, a pair of complementary flow paths which are hydraulically in parallel with an opening therebetween;

within said conduit means, a plurality of thin ribbon-like conductors which parallel each other i closely spaced relationship with each conductor passing through both of said flow paths and forming an electrically shorted turn linking said opening;

means for coupling a fluid flow through said conduit means from said inlet to said outlet with the fluid passing through the spaces between said conductors;

means for sensing the temperature of said fluid flow adjacent to said outlet;

an inductor providing a winding which, when energized, generates magnetic flux passing through said openings, which winding does not surround either of said flow paths;

means for energizing said inductor with alternating current at an adjustable power level thereby to induce local currents in said conductors;

feedback control means responsive to said sensing means for varying said power level as a function of the sensed temperature thereby to generate heat which is imparted to the fluid passing over said conductors and thereby maintain said sensed temperature substantially at a preselected level.

* * * * *